United States Patent [19]

Liang et al.

[11] Patent Number: 5,633,410

[45] Date of Patent: May 27, 1997

[54] PROCESS FOR THE CONVERSION OF 2,3-DIHYDROFURAN TO CYCLOPROPANECARBOXALDEHYDE

[75] Inventors: Shaowo Liang, Kingsport; Timothy W. Price, Church Hill, both of Tenn.

[73] Assignee: Eastman Chemical Company, Kingsport, Tenn.

[21] Appl. No.: 706,157

[22] Filed: Aug. 30, 1996

[51] Int. Cl.$^6$ .................................................. C07C 47/293
[52] U.S. Cl. .................................................. 568/443
[58] Field of Search .................................................. 568/443

[56] References Cited

U.S. PATENT DOCUMENTS 5,502,257  3/1996  Liang et al. .................................. 568/433

OTHER PUBLICATIONS

C. L. Wilson, J. Amer. Chem. Soc., 69, pp. 3002–3004 (1947).

*Primary Examiner*—Samuel Barts
*Attorney, Agent, or Firm*—J. Frederick Thomsen; Harry J. Gwinnell

[57] ABSTRACT

Disclosed is a process for the preparation of cyclopropanecarboxaldehyde by the isomerization of 2,3-dihydrofuran wherein 2,3-dihydrofuran is contacted with a catalyst selected from alumina, silica-alumina, silica, zirconia, titania and mixtures thereof having a nitrogen BET surface area of about 10 to 350 square meters per gram at elevated temperature.

7 Claims, No Drawings

PROCESS FOR THE CONVERSION OF 2,3-DIHYDROFURAN TO CYCLOPROPANECARBOXALDEHYDE

This invention pertains to a process for the preparation of cyclopropanecarboxaldehyde from 2,3-di-hydrofuran. More specifically, this invention pertains to the preparation of cyclopropanecarboxaldehyde by contacting 2,3-dihydrofuran with alumina at elevated temperatures.

Cyclopropanecarboxaldehyde and derivatives are important synthetic building blocks for introducing the cyclopropane group into chemical compounds useful as human and veterinary drugs and pesticides. See, for example, European Patent Publications EP 237,955 A2, EP 273,862 A2, EP 408,034 and EP 430,847 A1, Published PCT Application WO 91/09849, and U.S. Pat. No. 4,275,238.

The derivation of 2,3-dihydrofuran (2,3--DHF) from butadiene is described in U.S. Pat. No. 5,254,701. The overall scheme comprises the monoepoxidation of butadiene to produce 3,4-epoxy-1-butene which is rearranged to 2,5-dihydrofuran which then is rearranged to 2,3-DHF. 2,5-Dihydrofuran undergoes isomerization to 2,3-DHF in 96.1% yield via RuClH(CO)(Ph$_3$P)$_3$ catalysis at 65° C. in 2.5 hours. The initial steps, epoxidation and isomerization to 2,5-dihydrofuran, are described in U.S. Pat. Nos. 4,897,498 and 3,932,468.

The non-catalytic, thermal isomerization or rearrangement of 2,3-DHF to cyclopropanecarboxaldehyde (CPCA) at atmospheric pressure has been described by C. L. Wilson, *J. Amer. Chem. Soc.*, 69, pp. 3002-3004 (1947). The isomerization reported by Wilson consisted of passing 2,3-DHF through a column packed with broken glass and heated at 375°-540° C. Excessive residence times were used, resulting in low selectivities of CPCA, e.g., 10 to 40%, versus other products. The major byproducts were crotonaldehyde, carbon monoxide and propylene. The space-time yield was less than 25 g CPCA per liter-hour wherein the space-time yield is the grams of CPCA produced per liter of heated reactor space per hour. Wilson also reports that attempts to catalyze the conversion of 2,3-DHF to CPCA were not successful. For example, contacting 2,3-DHF with a nickel-copper catalyst gave no CPCA at all but, instead, propane and carbon monoxide and activated alumina caused complete decomposition, even at 200° C.

U.S. Pat. No. 4,275,238 describes a similar non-catalytic process using an open reactor instead of a packed column. The isomerization of 2,3-DHF takes place at 460°-480° C. and at atmospheric pressure. The conversion of 2,3-DHF on each pass was only in the range of 2-9%. The selectivity of the formation of CPCA versus crotonaldehyde was about 93%. Again, since the process is carried out in the absence of a catalyst under atmospheric pressure, the space-time yields are very low, i.e., only in the range of 30 to 80 g CCPA/L-hour. Prolonged heating results in the formation of byproduct crotonaldehyde which occurs via further isomerization of the product cyclopropanecarboxaldehyde.

U.S. Pat. No. 5,502,257 discloses a process for the preparation of CPCA by heating 2,3-DHF under superatmospheric pressure. The process is operated at a temperature of 300° C. to 600° C., preferably 350° C. to 550° C., and a pressure of 3 to 345 bars absolute, preferably 4.5 to 35.5 bars absolute and, most preferably 4.5 to 15 bars absolute.

We have discovered that 2,3-DHF may be converted to CPCA at lower temperatures, e.g., at temperatures lower than those utilized in the process of U.S. Pat. No. 5,502,257, by carrying out the isomerization reaction in the presence of a catalyst selected from alumina, silica-alumina, silica, zirconia, titania and mixtures thereof, wherein from about 3 to 30 mole percent of the 2,3-DHF is converted to CPCA per pass over the catalyst. Alternatively, when using the conditions according to U.S. Pat. No. 5,502,257, the rate of reaction of 2,3-DHF to CPCA may be increased by the use of the above-mentioned catalysts for the isomerization reaction. Thus, the present invention provides a process for the preparation of CPCA which comprises heating 2,3-DHF at a temperature of about 180° C. to 430° C. in the presence of a catalyst selected from alumina, silica-alumina, silica, zirconia, titania and mixtures thereof, wherein from about 3 to 30 mole percent of the 2,3-DHF is converted to CPCA per pass over the catalyst. The present process therefore provides a means for the synthesis of CPCA at lower temperatures and/or higher production rates per unit reactor volume (referred to herein as space-time yield defined as the grams of CPCA produced per liter of alumina catalyst). Such lower reaction temperatures reduce the fouling in the reactor and require less heat input per unit of reactor feed. Another advantage is that lower reaction temperatures can decrease the amount of CPCA that is converted to crotonaldehyde.

Although the novel isomerization process is believed to be operable over pressures of from about 1 to 345 bars absolute, pressures in the range of about 3 to 35.5 bars absolute are preferred with a range of 4.5 to 15 bars absolute being most preferred. We have found the rate of reaction of 2,3-DHF to CPCA is substantially higher at elevated pressure as compared to reaction rates at atmospheric pressure. It is also preferred to operate the process at temperatures in the range of about 200° C. to 350° C., and most preferably in the range of 200° C. to 300° C. when using the preferred alumina catalysts.

The process of this invention may be carried out in a batch, semi-continuous or continuous mode of operation. The process preferably is operated in a continuous mode using a gas phase reaction system wherein 2,3-DHF vapor is fed continuously to, and isomerization product comprising CPCA is continuously removed from, a heated reactor unit. The isomerization product removed from the reactor unit may be fed continuously to a distillation unit wherein the crude product is distilled to recover (1) the unreacted 2,3-DHF as the overhead product and (2) CPCA as an underflow stream from the bottom or base of the distillation column. The recovered 2,3-DHF may be returned to the reactor feed tank or used to manufacture other chemicals.

The purity of the 2,3-DHF used in the present invention is not an important factor in the conversion of 2,3-DHF to CPCA. For example, 2,3-DHF containing other components such as furan, tetrahydrofuran, 2,5-dihydrofuran or a mixture thereof in total amounts of up to 40 weight percent of the total weight of the 2,3-DHF feed material gives satisfactory results in terms of conversions and selectivities. The process also may be carried out using a gaseous 2,3-DHF feed which contains up to 95 volume percent of an inert gas such as nitrogen, hydrogen, helium, argon or carbon dioxide. Although the use of an inert gas is not essential, practical considerations such as the need to control reactor pressure may be facilitated by the use of an inert gas.

The rate of feed of 2,3-DHF in continuous, gas phase operation can be varied widely depending upon other process parameters such as the temperatures and pressures used and the degree of conversion desired. Gas hourly space velocities (GHSV—the unit volume of 2,3-DHF fed per unit volume of catalyst per hour) in the range of about 50 to 4600 may be used although GHSV values in the range of about 300 to 2500 are more typical.

The catalyst utilized in the present process is selected from alumina, silica-alumina, silica, zirconia, titania and mixtures thereof. The catalyst preferably is alumina or silica, most preferably alumina. The nitrogen BET surface area of the catalysts used in the process of our invention can vary substantially but normally is in the range of about 10 to 350 square meters per gram ($m^2/g$) with the range of about 30 to 300 $m^2/g$ being preferred. It is well known in the art that BET surface area is a function of crystalline phases and calcination history and should be as high as possible while maintaining the appropriate oxide phase. The catalysts may be used in the form of pellets, spheres, extrudates and the like. The particular form is not critical so long as the catalyst form does not lead to excessive channeling of the gaseous feed through the reactor, e.g., in continuous operation using a fixed bed of catalyst through which the reactant is passed. Preferably, the surface area:volume ratio of the catalyst is at least 500 and preferably greater than 1500. The crystalline phase of the alumina catalysts may be selected from the alpha, theta, delta, gamma, eta phases or a mixture of such crystalline phases.

The process of the invention is operated under a combination of conditions, e.g., temperature, pressure and residence time (GHSV), which results in about 5 to 30 mole percent of the 2,3-DHF being converted to CPCA per pass over the catalyst. A conversion of at least 5 mole percent is necessary to make the process feasible whereas conversions of 2,3-DHF to CPCA above about 30 mole percent result in increased formation of undesired byproducts. As mentioned above, the crude isomerization product comprising unreacted 2,3-DHF and CPCA may be removed from the reactor unit and fed to a distillation unit wherein the crude product is distilled to recover the unreacted 2,3-DHF as the overhead product. The recovered 2,3-DHF is recycled continuously to the reactor unit. The conversion of the 2,3-DHF to CPCA per pass in the process is at least 3 mole percent, preferably at least 5 mole percent. The conversion of about 3 to 30 mole percent of the 2,3-DHF to CPCA per pass over the catalyst distinguishes the present process from the aforementioned experiments performed by Wilson with activated alumina which resulted in complete destruction.

A preferred embodiment of the presence invention is a continuous process for the preparation of CPCA which comprises the steps of:

(1) continuously feeding a gaseous mixture comprising 2,3-DHF and an inert diluent in a 2,3-DHF:inert diluent volume ratio of about 1:0.01 to 1:10 to a reaction zone maintained at a temperature of about 200° C. to 300° C. and a pressure of about 4.5 to 35.5 bars absolute which reaction zone contains alumina catalyst having a BET surface area of about 30 to 300 square meters per gram; and (2) continuously removing a gaseous isomerization product comprising CPCA from the reaction zone;

wherein from about 5 to 30 mole percent of the 2,3-DHF is converted to CPCA per pass over the catalyst.

The novel process provided by the present invention is further illustrated by the following examples. The examples utilized a gas phase reaction unit consisting of a feed tank, a preheating line, a reactor constructed of stainless steel tubing 30 cm in length having an inside diameter of 2.5 cm and packed with 0.15 liter of alumina catalyst, a condenser and a receiver. The reactor was heated with an electric furnace. The pressure within the reactor was regulated by means of a back pressure regulator. Nitrogen was metered into the preheating line at a rate of 100 mL per minute. An even flow of 2,3-DHF having a purity of 99% was pumped from the feed tank into the preheating line wherein the mixture of 2,3-DHF and nitrogen was heated to about 100 to 200° C. and fed to the reactor. The 2,3-DHF:nitrogen volume ratio of the reactor feed gas was in the range of about 1:0.01 to 1:10. Temperatures within the reactor space were monitored by a thermowell containing two thermocouples which were placed 7.6 cm and 27 cm from the entrance to the heated section of the tube. The temperatures reported in the examples are averages of the two temperatures.

The isomerization product removed from the reactor was cooled by passing it through the condenser and collected in the receiver. This mixture was fed continuously to the mid-section of a distillation column. The base of the column was heated at 100° C. to 102° C. CPCA was recovered from the base of the column and unreacted 2,3-DHF was collected in a distillate receiver and continuously recycled to the feed tank.

The conversions and selectivities reported in the example were determined by gas chromatographic (GC) analyses performed on a Hewlett-Packard 5890 series II gas chromatography with a 30 meter DB-Wax and a 30 meter DB-17 capillary columns. The identities of the products obtained were confirmed by nuclear magnetic resonance spectrometry and gas chromatography-mass spectrometry comparing the spectra to those of authentic samples purchased from Aldrich Chemical.

The alumina catalysts employed in the examples were selected from the commercial materials set forth below wherein BET SA is the nitrogen BET surface area [Brunauer, S., Emmet, P.H., and Teller, E., J. Am. Chem. Soc., 60, 309–16 (1938)] which is given in square meters per gram.

| | ALUMINA CATALYSTS | |
|---|---|---|
| Catalyst No. | Tradename | BET SA |
| I | Norton SA 6276 | 220–270 |
| II | Harshaw Al-0104T | 80–100 |
| III | Calsicat E-149 SD | 39 |
| IV | Norton SA 5252 | 0.2–0.5 |
| V | Norton SA 5205 | 0.057 |

EXAMPLES 1–3 AND COMPARATIVE EXAMPLES 1–5

2,3-DHF was isomerized according to the procedure described above at atmospheric pressure using different temperatures and alumina catalysts and a 2,3-DHF feed rate of 1.9 g 2,3-DHF per minute. The experiments constituting Examples 1–4 and Comparative Examples 1–5 were carried out for a sufficient length of time to attain steady-state conditions. The results obtained in these examples are set forth in Table I wherein "Cat" is the alumina catalyst set forth above which was used in the experiment, "Temp" is the average temperature described above in ° C. at which the experiment was carried out, "STY" is the space-time yield defined as the grams of CPCA produced per liter of CATA-LYST per hour, "2,3-DHF Conv" is the mole percent conversion of 2,3-DHF defined as:

$$\frac{\text{Moles 2,3-DHF converted to products}}{\text{Moles 2,3-DHF fed}} \times 100$$

and "CPCA Select" is the mole percent selectivity to CPCA defined as:

$$\frac{\text{Moles 2,3-DHF converted to CPCA}}{\text{Moles 2,3-DHF converted to CPCA + HCr}} \times 100$$

wherein HCr is crotonaldehyde.

TABLE I

| Example | Cat | Temp | 2,3-DHF Conv | CPCA Select | STY |
|---|---|---|---|---|---|
| 1 | I | 232 | 14 | 99 | 61 |
| 2 | II | 240 | 7 | 97 | 27 |
| 3 | III | 243 | 6 | 98 | 28 |
| C-1 | IV | 340 | 0 | — | 0 |
| C-2 | IV | 407 | 8 | 93 | 59 |
| C-3 | IV | 419 | 18 | 92 | 126 |
| C-4 | V | 340 | 0 | — | 0 |
| C-5 | V | 423 | 11 | 97 | 78 |

EXAMPLES 4–6 AND COMPARATIVE EXAMPLES 6–9

The procedure described in the preceding examples is repeated for the isomerization of 2,3-DHF to CPCA at different temperatures using different alumina catalysts a pressure of 4.5 bar absolute and a 2,3-DHF feed rate of 10.2 g per minute. The results obtained in Examples 4–6 and C–6 to C–9 are set forth in Table II wherein "Cat", "Temp", "STY", "2,3-DHF Conv" and "CPCA Select" have the meanings given above.

TABLE II

| Example | Cat | Temp | 2,3-DHF Conv | CPCA Select | STY |
|---|---|---|---|---|---|
| 4 | I | 200 | 15 | 100 | 404 |
| 5 | II | 220 | 15 | 98 | 392 |
| 6 | III | 210 | 12 | 99 | 343 |
| C-6 | IV | 340 | 0 | — | 0 |
| C-7 | IV | 380 | 15 | 95 | 581 |
| C-8 | V | 340 | 0 | — | 0 |
| C-9 | V | 394 | 12 | 93 | 446 |

COMPARATIVE EXAMPLES 10–16

The procedure described above for Examples 1–3 is repeated for the isomerization of 2,3-DHF to CPCA at different temperatures except that the reactor is packed with quartz chips rather than alumina catalyst. The results obtained in Comparative Examples 10–16 are set forth in Table III wherein "Temp", "STY", "2,3-DHF Conv" and "CPCA Select" have the meanings given above.

TABLE III

| Comparative Example | Cat | Temp | 2,3-DHF Conv | CPCA Select | STY |
|---|---|---|---|---|---|
| C-10 | None | 232 | 0 | — | 0 |
| C-11 | None | 240 | 0 | — | 0 |
| C-12 | None | 243 | 0 | — | 0 |
| C-13 | None | 340 | 0 | — | 0 |
| C-14 | None | 407 | 3 | 97 | 21 |
| C-15 | None | 419 | 4 | 95 | 26 |
| C-16 | None | 423 | 5 | 95 | 38 |

COMPARATIVE EXAMPLES 17–22

The procedure described above for Examples 4–6 is repeated for the isomerization of 2,3-DHF to CPCA at different temperatures except that the reactor is packed with quartz chips instead of alumina catalyst. The results obtained in Comparative Examples 17–22 are set forth in Table V wherein "Temp", "STY", "2,3-DHF Conv" and "CPCA Select" have the meanings given above.

TABLE V

| Comparative Example | Cat | Temp | 2,3-DHF Conv | CPCA Select | STY |
|---|---|---|---|---|---|
| C-17 | None | 200 | 0 | — | 0 |
| C-18 | None | 220 | 0 | — | 0 |
| C-19 | None | 210 | 0 | — | 0 |
| C-20 | None | 340 | 0 | — | 0 |
| C-21 | None | 380 | 2 | 99 | 68 |
| C-22 | None | 394 | 2 | 97 | 94 |

The invention has been described in detail with particular reference to preferred embodiments thereof, but it will be understood that variations and modifications can be effected within the spirit and scope of the invention.

We claim:

1. Process for the preparation of cyclopropanecarboxaldehyde which comprises heating 2,3-dihydrofuran at a temperature of about 180° C. to 430° C. in the presence of a catalyst selected from alumina, silica-alumina, silica, zirconia, titania and mixtures thereof, wherein the nitrogen BET surface area of the catalyst is in the range of about 10 to 350 square meters per gram and from about 3 to 30 mole percent of the 2,3-DHF is converted to CPCA per pass over the catalyst.

2. Process according to claim 1 wherein the temperature is in the range of about 200° C. to 350° C. and the pressure is in the range of about 3 to 35.5 bars absolute.

3. Process according to claim 2 wherein the catalyst is selected from alumina and silica and has a nitrogen BET surface area of about 30 to 300 square meters per gram.

4. Process according to claim 3 wherein the catalyst is alumina.

5. Continuous process for the preparation of cyclo- propanecarboxaldehyde which comprises the steps of:

(1) continuously feeding a gaseous mixture comprising 2,3-DHF and an inert diluent in a 2,3-DHF:inert diluent volume ratio of about 1:0.01 to 1:10 to a reaction zone maintained at a temperature of about 200° C. to 300° C. and a pressure of about 4.5 to 35.5 bars absolute which reaction zone contains a catalyst selected from alumina, silica-alumina, silica, zirconia, titania and mixtures thereof having a nitrogen BET surface area of about 30 to 300 square meters per gram; and (2) continuously removing a gaseous isomerization product comprising cyclopropanecarboxaldehyde from the reaction zone;

whereby about 5 to 30 mole percent of the 2,3-DHF is converted to CPCA per pass over the catalyst.

6. Process according to claim 5 wherein the gas hourly space velocity of the 2,3-dihydrofuran feed is in the range of about 300 to 2500.

7. Process according to claim 6 wherein the catalyst is alumina.

* * * * *